(12) United States Patent
Andrinal Lopez et al.

(10) Patent No.: US 11,819,871 B2
(45) Date of Patent: Nov. 21, 2023

(54) WEARABLE ELECTRONIC SUBSTANCE DISPENSER WITH INTERCHANGEABLE PARTS AND OPERATING METHOD

(71) Applicant: Inentia Aro SL, Madrid (ES)

(72) Inventors: Daniel Andrinal Lopez, Madrid (ES); Ramón Ignacio Cisneros De Los Arcos, Madrid (ES); Helga Seyler', Madrid (ES)

(73) Assignee: INENTIA ARO SL, Madrid (ES)

( * ) Notice: Subject to any disclaimer, the term of this patent is extended or adjusted under 35 U.S.C. 154(b) by 254 days.

(21) Appl. No.: 17/267,169

(22) PCT Filed: Aug. 7, 2019

(86) PCT No.: PCT/ES2019/070555
§ 371 (c)(1),
(2) Date: Feb. 9, 2021

(87) PCT Pub. No.: WO2020/030839
PCT Pub. Date: Feb. 13, 2020

(65) Prior Publication Data
US 2021/0283627 A1    Sep. 16, 2021

(30) Foreign Application Priority Data

Aug. 10, 2018   (ES) ............................... ES201830818

(51) Int. Cl.
*B05B 9/08*        (2006.01)
*A44C 5/20*        (2006.01)
(Continued)

(52) U.S. Cl.
CPC .............. *B05B 9/08* (2013.01); *A44C 5/0007* (2013.01); *A45D 34/02* (2013.01); *A45D 2034/005* (2013.01)

(58) Field of Classification Search
CPC ........................... A44C 5/0023; A44C 15/002
See application file for complete search history.

(56) References Cited

U.S. PATENT DOCUMENTS

| 4,972,684 A | 11/1990 | Aitken |
| 5,217,143 A | 6/1993 | Aikten |

(Continued)

FOREIGN PATENT DOCUMENTS

| CN | 204166295 U | 2/2015 |
| CN | 204273575 U | 4/2015 |

(Continued)

*Primary Examiner* — Jack W Lavinder
(74) *Attorney, Agent, or Firm* — Gerald R. Prettyman

(57) ABSTRACT

Disclosed are methods and wearable electronic devices for dispensing substances, it being possible to release the substances by means of a diffuser or atomiser system. The device, which has a function that allows the wearing of swappable capsules containing substances, comprises specific connectors that allow the complete modularity of the capsules, of the display/control pane and of the straps, thereby permitting the device to be fully personalised and optimised. The tightening/loosening and attachment system allows the device to be secured to a body automatically and intuitively. Of note is the inclusion of motors, sensors, readers and antennas in the system, which allow sensory impact to be integrated into the use experience (emission of visual, haptic or olfactory signals). In addition, communication and identification systems integrated into the elements provide interoperability between same, with other devices and between users.

1 Claim, 7 Drawing Sheets

(51) Int. Cl.
    *A45D 34/00*     (2006.01)
    *A44C 5/00*     (2006.01)
    *A45D 34/02*     (2006.01)

(56) References Cited

U.S. PATENT DOCUMENTS

| | | |
|---|---|---|
| 6,223,744 B1 | 5/2001 | Garon |
| 8,925,833 B2 | 1/2015 | Ki et al. |
| 8,950,238 B2 | 2/2015 | Shaw et al. |
| 8,991,722 B2 | 3/2015 | Friend et al. |
| 11,154,126 B1 * | 10/2021 | Zheng .................. A61J 7/0076 |
| 2007/0279852 A1 | 12/2007 | Daniel |
| 2015/0212541 A1 | 7/2015 | Lu |
| 2016/0058375 A1 | 3/2016 | Rothkopf |
| 2020/0245822 A1 * | 8/2020 | Chacon, Jr. ............. G04G 17/08 |
| 2021/0402037 A1 * | 12/2021 | Kearney ................. B05B 12/12 |

FOREIGN PATENT DOCUMENTS

| | | |
|---|---|---|
| ES | 2335375 A1 | 3/2010 |
| ES | 2655309 A1 | 9/2018 |
| GB | 2536911 A | 10/2018 |
| JP | 2017221640 A | 12/2017 |
| KR | 20180001767 U | 6/2018 |
| WO | 2009019797 A1 | 2/2009 |
| WO | 2014012486 A1 | 1/2014 |
| WO | 2014015031 A1 | 1/2014 |
| WO | 2015189866 A1 | 5/2016 |
| WO | 2018004685 A1 | 1/2018 |

\* cited by examiner

WEARABLE ELECTRONIC SUBSTANCE DISPENSER WITH INTERCHANGEABLE PARTS AND OPERATING METHOD

CROSS-REFERENCE TO RELATED APPLICATION

This application is a U.S. National filing of PCT/ES2019/070555, filed 7 Aug. 2019 which claims priority to P201830818 (ES) filed 10 Aug. 2018 and is titled, "Dispositivo Electrónico Vestible Dispensador De Sustancias Con Elementos Intercambiables Y Método De Funcionamiento."

STATEMENT REGARDING FEDERALLY SPONSORED RESEARCH OR DEVELOPMENT

Not Applicable

BACKGROUND OF THE INVENTION

Field of Invention

This patent belongs to the functional jewellery sector. It refers to an electronic device and to a method for activating different methods for the smart dispensing of substances through spray mechanisms built into the wearable device. The components of the device include one or several interchangeable capsules that can contain one or several substances, a base, a processor to control the operation of the device, an interchangeable display and control panel, connectors and straps for the transfer of data, power, and substances contained in the capsules, along with a dispenser system (diffusion/atomisation), and a personalised tightening/loosening and securing system. In terms of the device, the personalisation, optimisation and exchange of parts is possible thanks to removable and interchangeable connectors and electronic components. The method also includes the dispensing procedure and the interoperability of the various electronic components and of the system with other devices using connectivity elements.

DESCRIPTION OF RELATED ART

Jewellery includes more or less valuable items that are used to adorn the body. It is normally made of some kind of noble metal and is sometimes decorated with pearls or gemstones, which have been used by mankind for over 100.00 years by every culture around the world. The most noteworthy items of jewellery include necklaces, bracelets, bangles, hoops, rings, buckles, and hair ornaments, among others. Although, in the past, jewellery has been used for merely ornamental purposes, there has been a new trend in recent years towards the use of smart functions to make the everyday lives of users easier. This application of wearable technology has already taken root in many different industrial sectors, such as the textile or watchmaking sectors, logically arising from the development of new technologies in these areas.

Furthermore in ancient times, perfumes were primarily used as offerings in rituals or simply for personal hygiene purposes to provide their users or their environment with certain scents. The evolution of perfumes has to date focused primarily on the aromatic ingredients used. Furthermore, their application to the body has been restricted to atomisation from an eye-catching bottle. Nowadays, decorative wearables are available that offer the function of releasing fragrances, although they incorporate no or almost no smart technologies for their application and their personalisation is limited.

During the 20th century and what we have seen of the 21st century so far, the jewellery and the perfume sectors have strengthened their positions as industries that produce billions of euros in product sales. Their only recent innovations are based on the appearance of the decorative elements, the appearance of the traditional bottles, or the composition of the fragrant substances. Any functional aspects have been ignored, and both technical sectors have seemingly come to a standstill when it comes to development and innovation.

There are now systems that describe wearables used to released atomised liquids in the cosmetics and perfume sector. These often contain the spray system in the ornamental elements, are limited in terms of functionality, cannot be overly personalised, and offer limited dispensing control or are rather large in size (see, for example, U.S. Pat. No. 4,972,684, ES2335375A1, U.S. Pat. No. 5,217,143A, WO2015189866A1). In addition, they are mostly limited to a mechanical system and require the full attention and intention of the user to apply the substance according to their own perception, criteria, or environment (impact, volume, persistence, etc.). These wearable devices do not allow for information to be transferred between the user and the device, or between the liquid to be atomised and its environment, in order to optimise, control or personalise the dispensing or appearance of the device. Innovations in liquid atomisation technologies in portable devices for inhalation therapies (for example, asthma, Chronic Obstructive Pulmonary Disease COPD, etc.) or cosmetics focus on their miniaturisation for improved portability and/or on the liquid release mechanisms, without meeting the needs of fashion, personalisation capacities, comfort and functions to supplement wearable technology (for example, U.S. Pat. No. 8,991,722B2, U.S. Pat. No. 8,925,833B2, WO2009/019797A1). The most relevant invention in this regard might be the wearable aerosol dispenser (U.S. Pat. No. 6,223,744B1) that consists of a case, an aerosol reservoir, a pressurised dispensing mechanism, a fastening component, and a filling mechanism. This appliance is designed solely as a nasal/oral inhaler, with no fashionable functions or connectivity, and limited smart functions for the application. For example, this device has no capacity to personalise the liquid or the dose to be supplied in line with real-time health monitoring, the programming of application alerts, ingredient personalisation system, or automatic or semi-automatic release. Furthermore, the screen on the device only displays information. Furthermore, liquid dispensing devices from this invention also have the disadvantage of needing to remove the strap from the user's wrist in order to refill the liquid or to exchange the reservoir containing the substance. Perhaps another patent that is technically closer to this invention is national patent application ES2655309A1 in which the invention describes a bracelet with personalisable cover plates, which consists of a frame or connection system, a fragrant liquid reservoir contained in the cover plates, and several release mechanisms. This invention has no reservoir, or the capacity to transfer information once it has been internally processed, nor does it have any type of automatic or (semi) automatic or remote electronic or operating control for the device or its release mechanisms, nor does it include sensors among its components or any method or part to receive, view or generate electronic information. The device does not allow for an analysis of the environment (epidermis, environmental, etc.) to optimise liquid application. Other patented wearable devices offer new systems for permanent interaction with the user and with other devices to make time administration easier, monitor health and fitness parameters, and record or play back audio, among other applications (for example, US2016/0058375A1, WO2014015031A1). Furthermore, in some versions, these devices might provide functions for the removal or interchange of independent modules and electronic components attached to a mount to adapt to user needs (battery charging, comfort, appearance, functionality). However, the mechanism for fitting and removing certain traditional electronic parts is complicated or impossible, making their replacement or the replacement of internal components difficult. Although there are patents that describe a modular system of wearable devices with units for their personalisation, such as patents US2007/0279852, WO2014/012486 A1 or CN204273575U, these do not have substance dispensing and portability capacity. Another specific case of interest is the odour removing device (U.S. Pat. No. 8,950,238B2), which consists of an electronic device equipped with sensors and capable of emitting a fragrance in a controlled and/or continuous manner in line with physical parameters detected. This invention is not applied as a fashionable decorative item or as a substance wearable, and its appearance or that of the substance to be dispensed cannot be personalised. Another specific case of interest is the invention of a display that is separable from a mount (WO2018/004685A1) and/or from the battery (US2015/0212541 A1) in an electronic wearable, although this function merely seeks to improve the battery charging mechanism and the comfort of the wearable. The concept of separating the display panel from the central control unit and from its battery is unprecedented in a wearable, and makes the interchange of internal parts and the personalisation and repair of the device easier. Another point to consider in current substance dispensing wearables is the need for a smart fastening/adjustment system for the sensors to work correctly and for greater wearing comfort.

As a result, there is currently the need for a wearable device with a moveable holder for capsules containing one or several substances, with the capacity to connect and disconnect parts and the capacity for smart fastening/adjustment for increased personalisation of use and appearance, which contains a smart substance dispensing system for intuitive use and dispensing scheduling, user connectivity, and interoperability with the environment. The following references were used when drafting this patent:

U.S. Pat. No. 4,972,684 with priority date 10 Apr. 1989 "Bangle having removable atomizer and interchangeable decorative clips" (Alexander G. Aitken).

ES2335375A1 with priority date 23 Jul. 2007 "Bangle dispensing perfume convertible to a perfume-dispensing bracelet" (Manuel González Pérez).

WO2015189866 with priority date 12 Jun. 2014 "Wrist diffuser, particularly for the diffusion of perfumed fragrances".

U.S. Pat. No. 5,217,143A with priority date 9 Aug. 1991 "Actuating device for a self-contained fluid dispenser in a bangle" (Alexander G. Aikten).

US8991722B2 with priority date 11 May 2011 "Microfluidic apparatus for the atomization of a liquid" (James Friend, Leslie Yei, David Morton, Michelle McIntosh, Aisha Qi, Jenny Ho, Anushi Rajapaksa).

U.S. Pat. No. 8,925,833B2 with priority date 26 Jul. 2010 "Portable electric mist supply apparatus for liquid cosmetics" (Joong-Hyung Ki, Su-Jin Son, Sung-Sin Kim).

CN204273575U with priority date 22 Apr. 2015 "Portable perfume atomizing sprayer" (Liu Yajun).

WO2009019797A1 with priority date 7 Aug. 2007 "Portable ultrasonic mist generator" (Yoshimitsu Konishi, Makiko Konishi).

US6223744B1 with priority date 16 Mar. 1999 "Wearable aerosol delivery apparatus" (Mark Garon).

ES2655309A1 with priority date 19 Aug. 2016 "Bracelet with personalisable cover plates" (Ramón Ignacio Cisneros de los Arcos, Daniel Andrinal López).

US20070279852A1 with priority date 27 Feb. 2004 "Wearable modular interface strap" (Simon R. Daniel).

WO2014012486A1 with priority date 17 Jul. 2012 "Wearable wireless intelligent electronic device having removable and freely-combinable functional modules" (Gao Shouqian, Shi Zhuhong).

CN204166295U with priority date 31 Oct. 2014 "Intelligent bracelet watch with expandable function modules" (Zhang Bokai; Liang Bairong).

WO2014015031A1 with priority date 17 Jul. 2012 "Time Cycle Audio Recording Device" (Mike Sarow and Matthew R. Dooley).

US20160058375A1 with priority date 2 Sep. 2014 "Wearable electronic device" (Fletcher R. Rothkopf).

WO2018004685A1 with priority date 1 Jul. 2016 "Separable wearable device" (Joyce Cumming Weiner).

US20150212541A1 with priority date 29 Jan. 2014 "Wearable electronic device" (Wen Ting Lu).

U.S. Pat. No. 8,950,238B2 with priority date 31 Aug. 2012 "Odor removing device" (Stephen H. Shaw, Rachid M. Alameh, William P. Alberth, Jerome Vodges).

SUMMARY OF THE INVENTION

Methods and wearables are presented to dispense substances, with which these substances can be released through an atomiser or diffuser system. The device, which acts as a holder for the interchangeable capsules containing substances, is formed by specific connectors to ensure the entirely modular nature of the capsules, of the display/control panel, and of the straps for full personalisation and optimisation of the device Its tightening/loosening and securing system means that it is secured to a body both automatically and intuitively. The incorporation of motors, sensors, readers and antennas into the system must be highlighted, which means that sensory-based impact can be integrated into the user experience (emitting of visual, tactile or olfactory signals). The communication and identification systems integrated into the parts also provide interoperability between them, with other devices, and between users.

DETAILED DESCRIPTION OF THE INVENTION

The objects, characteristics and advantages of this invention will be made clear in the following detailed description. However, it must be remembered that the detailed description and the examples given are for illustrative purposes only, despite indicating specific versions of the invention, as different changes and modifications within the spirit and scope of the invention will be clear to experts in the field based on this detailed description.

This invention combines several concepts: a wearable substance receptacle and dispenser, a smart electronic device and a decorative capsule holder that is both wearable and personalisable. Furthermore, the invention describes a method for dispensing substances, which allows for the complete personalisation of the use and appearance of the device (information displayed on display/control panel, device appearance and dispensing) and the use and personalisation of different connectivity functions. The electronic components of the device allow for controlled dispensing of the substance(s) contained in the capsules, and have a sensory-based impact on the user experience (through the output of visual, tactile and olfactory signals and/or a combination thereof) which provide greater personalisation for use and for the device in itself, in comparison with prior inventions.

Figure 1:
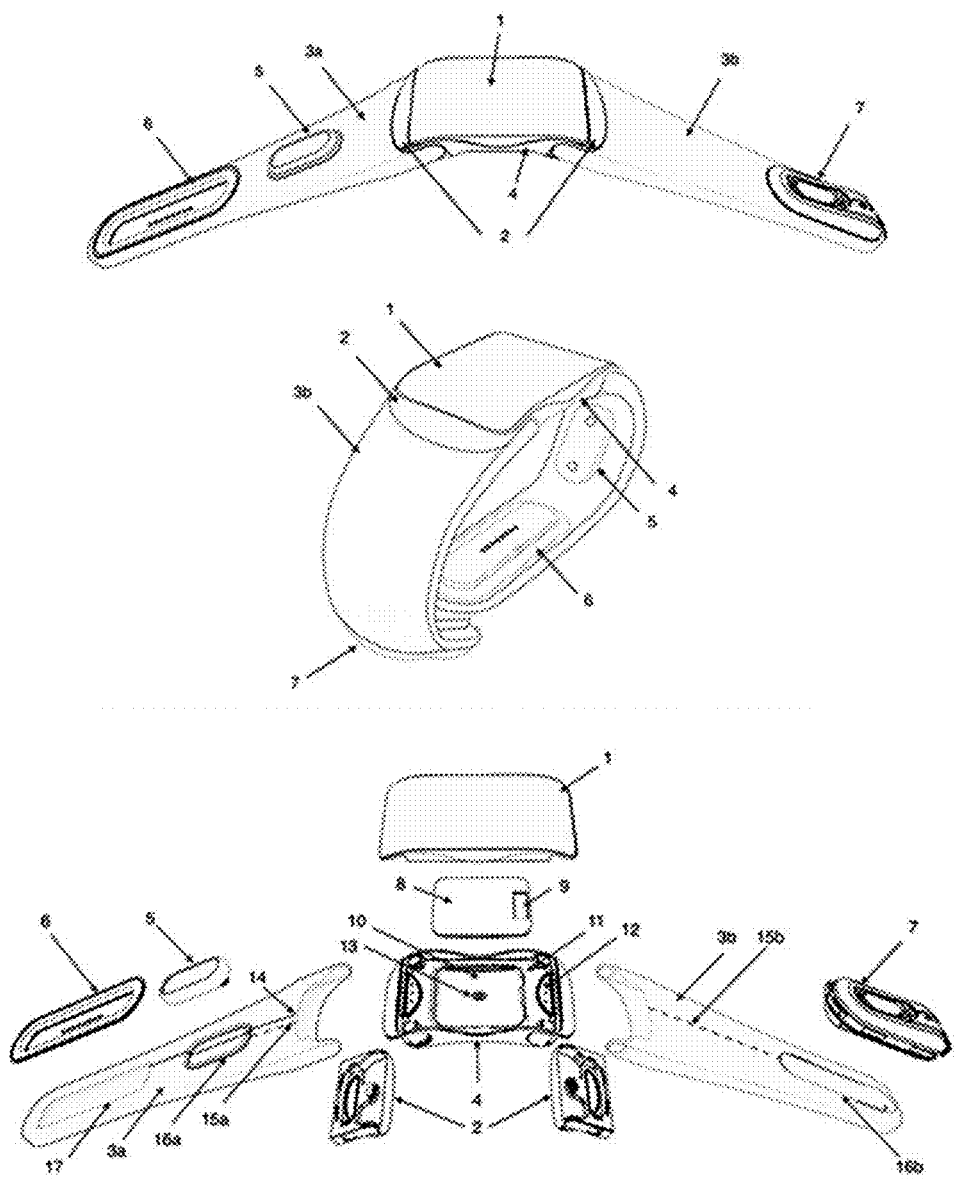
FIG. 1 Device open, closed, and exploded with its components in an isometric view.

The most innovative parts of the device in relation to devices and inventions found in the background information are described below:

Shown in FIG. 1 are: 1. Interchangeable display/control panel; 2. Base-strap connector; 3a. Primary strap; 3b. Secondary strap; 4. Base; 5. and 8. Interchangeable capsules; 6. Tightening/loosening and securing system stator; 7. Substance dispenser. Atomiser; 9. Capsule data communication/identification/storage system; 10 and 16a. Recesses for connection of the interchangeable capsules; 11. Recess for connection of the display/control panel; 12. Connection and coupling between the base and the display/control panel; 13. Connection and coupling system between the base and the capsule; 14., 15a. and 15b. Connection inside the straps; 16a. and 16b. Recesses for connection of the substance dispenser system; and 17. Recess where the stator is located.

Figure 2:
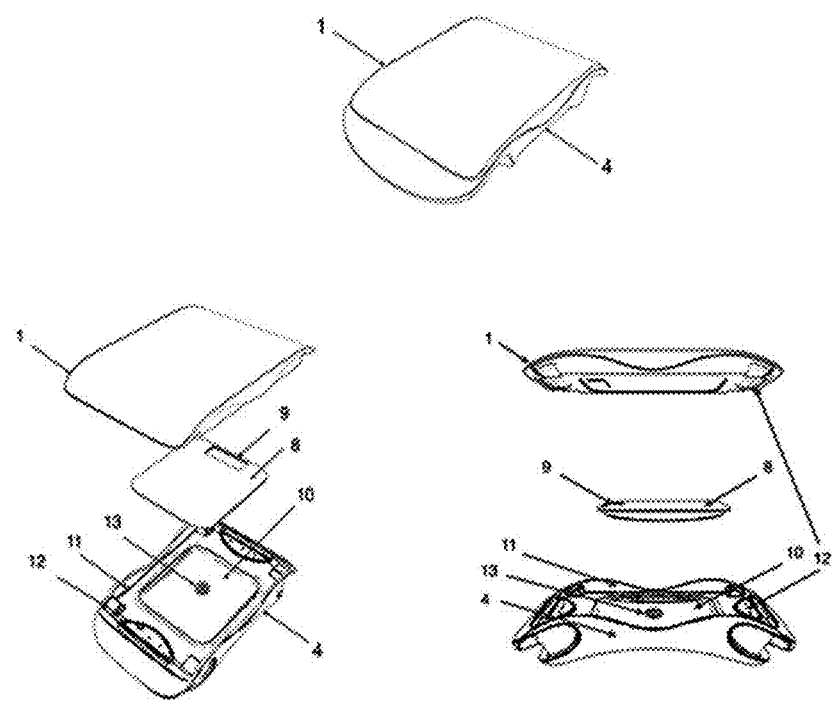
FIG. 2 Capsule, base, and display/control panel of the device (open and closed) showing capsule replacement in an isometric view.

Shown in FIG. 2 are: 1. Interchangeable display/control panel; 4. Base; 8. Interchangeable capsule; 9. Capsule data communication/identification/storage system; 10. Recess for connection of the interchangeable capsule; 11. Recess for connection of the display/control panel; 12. Connection and coupling between the base and the display/control panel; and 13. Connection and coupling system between the base and the capsule.

Figure 3:
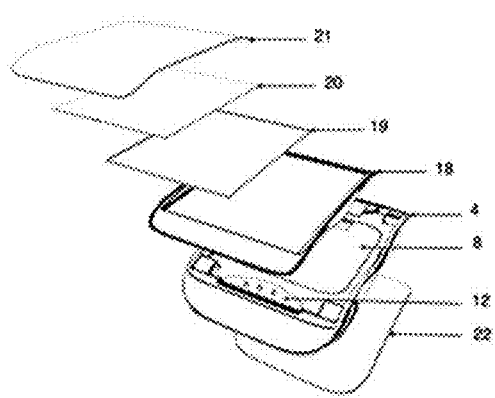
FIG. 3 Display/control panel and base of the device with their components exploded in an isometric view.

Shown in FIG. 3 are: 4. Base; 8. Interchangeable capsule; 12. Connection and coupling between the base and the display/control panel; 18. Display/control panel mount; 19. Lighting panel; 20. Digitiser; 21. Protective surface; and 22. Battery charging surface.

Figure 4:
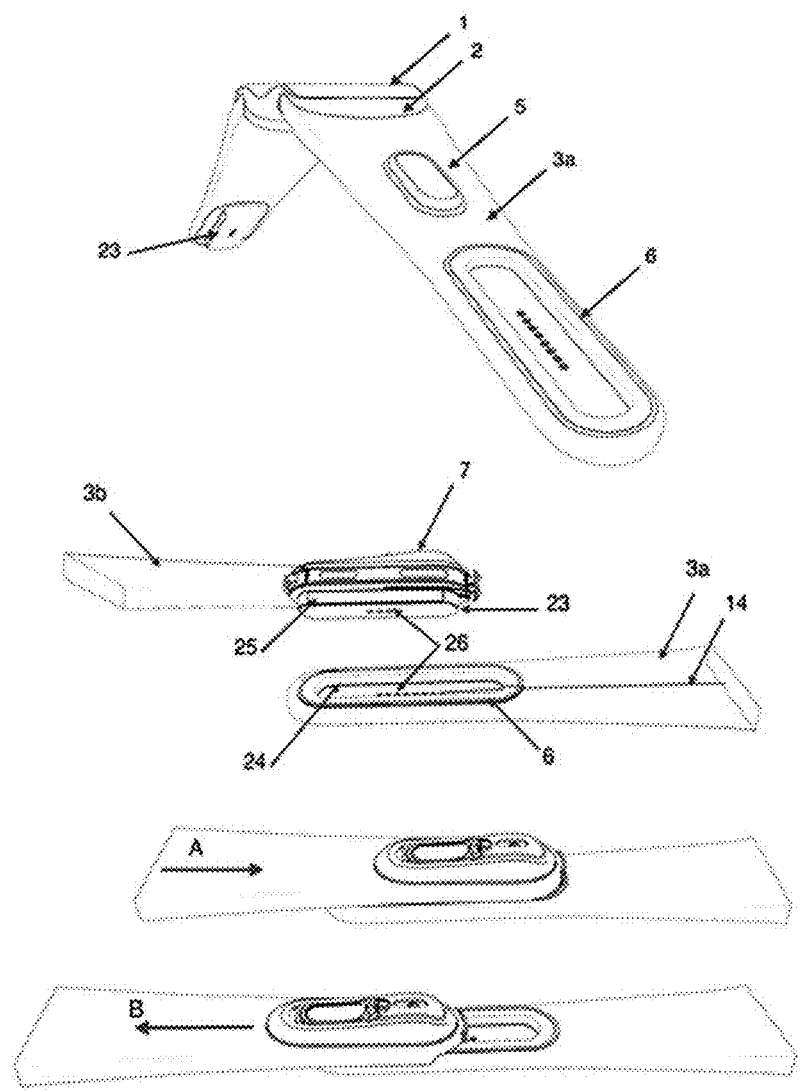
FIG. 4 Device tightening/loosening and securing system showing all its parts in perpendicular and asymmetric view.

Shown in FIG. 4 are: 1. Interchangeable display/control panel; 2. Base-strap connector; 3a. Primary strap; 3b. Secondary strap; 5. Interchangeable capsule; 6. Tightening/loosening and securing system stator; 7. Substance dispenser. Atomiser; 14. Electrical connection inside the strap; 23. Tightening/loosening and securing system track, and atomiser mount; 24. and 25. Tightening/loosening and securing system actuators; and 26. Connection between the securing system stator and track; A, B. Method of action. A. Tightening. B. Loosening.

Shown in FIG. 4 are: 1. Interchangeable display/control panel; 2. Base-strap connector; 3a. Primary strap; 3b. Secondary strap; 5. Interchangeable capsule; 6. Tightening/loosening and securing system stator; 7. Substance dispenser. Atomiser; 14. Electrical connection inside the strap; 23. Tightening/loosening and securing system track, and atomiser mount; 24. and 25. Tightening/loosening and securing system actuators; 26. Connection between the securing system stator and track; A, B. Method of action A. Tightening. B. Loosening.

Figure 5:
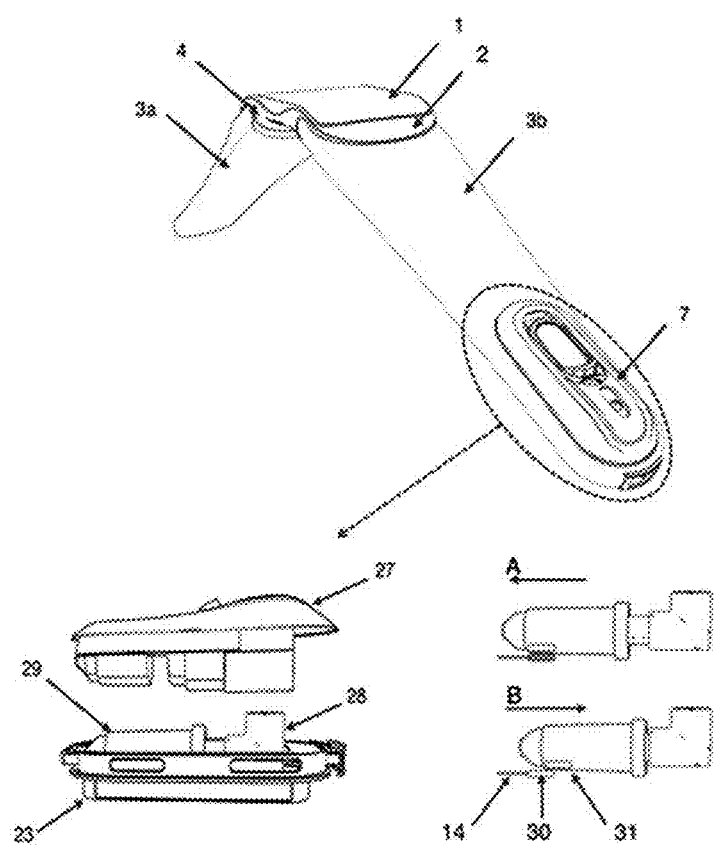
FIG. 5 DIRECT MODE substance dispenser of the device Part location and atomiser operations are described for a specific version.

Shown in FIG. 5 are: 1. Interchangeable display/control panel; 2. Base-strap connector; 3a. Primary strap; 3b. Secondary strap; 7. Substance dispenser. Atomiser; 14. Electrical connection inside the strap; 23. Tightening/loosening and securing system track, and atomiser mount; 27. Atomiser housing; 28. Atomiser actuator; 29. Atomiser unit; 30. Electromagnet; 31. Magnet; A, B. Methods of action. A. Standby B. Atomisation.

Figure 6:
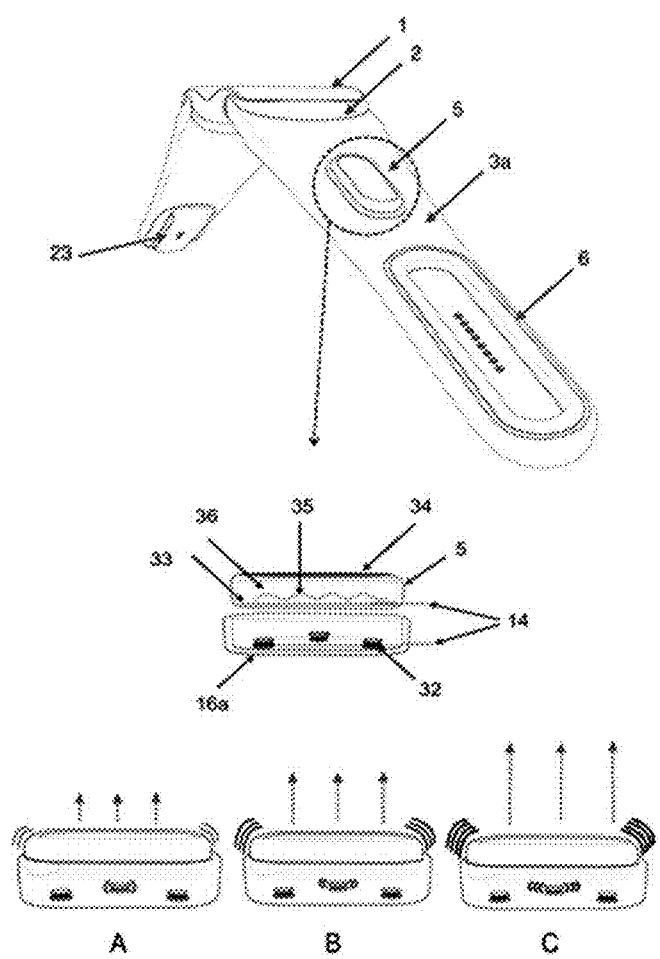
FIG. 6 INDIRECT MODE substance dispenser of the device. Part location and diffuser operations are described for a specific version.

Shown in FIG. 6 are 1. Interchangeable display/control panel; 2. Base-strap connector; 3a. Primary strap; 5. Interchangeable capsule; 6. Tightening/loosening and securing system stator 16a. Recess for connection of the interchangeable capsule of the strap; 32. Motor; 33. Piezoelectric substrate; 34. Membrane; 35. Ultrasound waves symbol; 36. Substance; A, B, C. Particle propellant modes depending on signal intensity and frequency; A. Low. B. Medium. C. Strong.

Interchangeable capsules. The capsules (8, 5—FIG. 1) for the device can be made of a polymer, ceramic, glass, metal, composite, single, or multilayer material or a combination of materials, with mechanical and chemical resistance to store the substance(s) in liquid, solid or gaseous state. The inside of the capsule may be segmented and contain one or several substances. The substance is extracted from the interchangeable capsule (8—FIG. 1) and is channeled towards the base of the device (4—FIG. 1) through a lid-connector with closure, connection, and/or a non-drip valve. Another interchangeable capsule (5—FIG. 1) may also contain substances independently or be connected through the base of the device and through an internal connection of the strips (15a—FIG. 1) with one or several substances contained in the first interchangeable capsule (8—FIG. 1).

These interchangeable capsules can incorporate a data communication/identification/storage system (9—FIG. 1), such as a chip, RFID tag or similar, where information is stored and is read by a reader and processed by the processor, both of which can be located in the base (4—FIG. 1) of the device. For example, the chip in the capsule may contain information to be displayed on the display/control panel (1—FIG. 1) of the device (designs, digital image, content, etc.) (FIG. 9) or other device (FIG. 8), or may contain means of electronic identification as part of an electronic security system to avoid system falsification.

Figure 8:
FIG. 8 Graphic representation of an example of interoperability between systems, user and environment, data transfer, and software processing via a remotely connected device.
Figure 9:
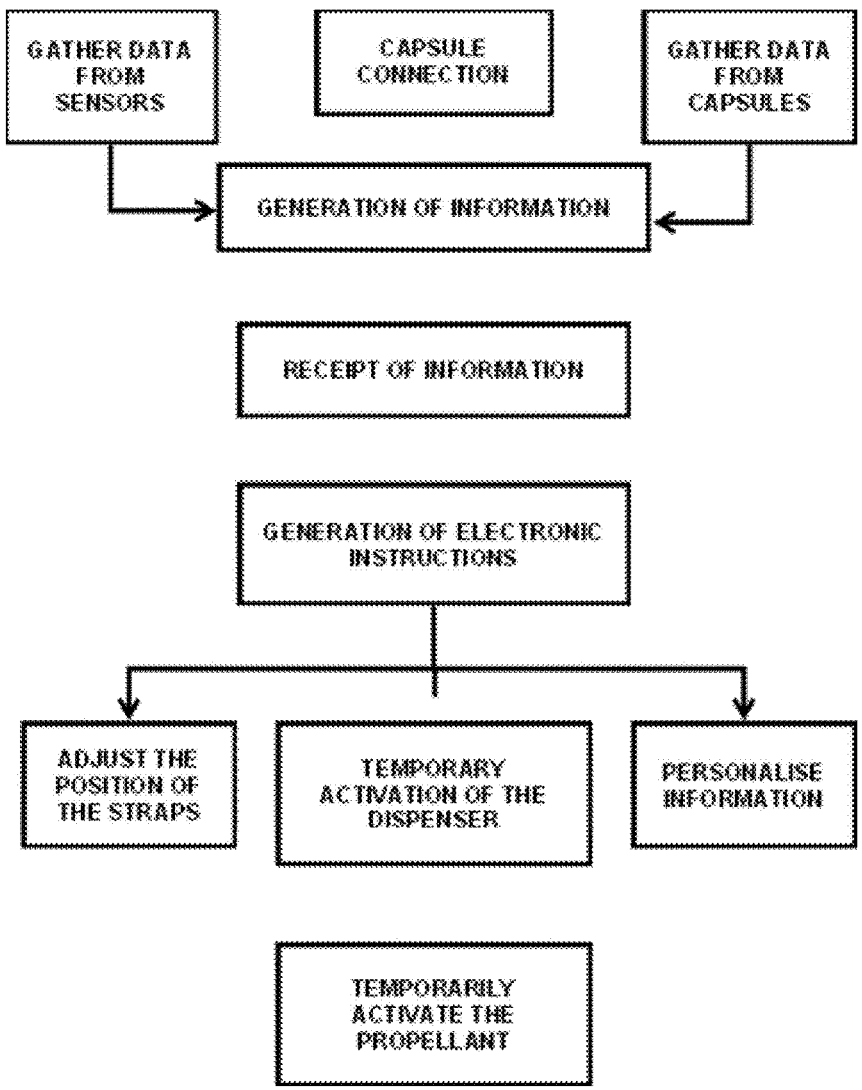
FIG. 9 Flowchart describing the possible operations of a method to dispense substances contained in interchangeable capsules using a wearable device.

Base. The base (4—FIG. 1) of the device, to which the interchangeable capsule (8—FIG. 1) containing one or several substances and the interchangeable display/control panel (1—FIG. 1) are connected. This base also incorporates the substance flow connection between the capsule (8—FIG. 1) and the straps (3a, 3b—FIG. 1), and a physical connection (12—FIG. 1) to connect and disconnect the display/control panel (1—FIG. 1). It may also contain integrated circuit boards, a processor or microcontroller, a memory, a battery, and/or power generator, the electronic connection from the motherboard and battery to the components of the device, other chips or circuits, data and wave transmission parts, and sensors. Examples of data and wave transmission parts include sensors and connectivity components, such as telephone antenna, microphones, speakers, tactile devices, RFID reader, etc. Examples of sensors include those helping with the smart application of substances, such as pH sensors, temperature sensors, electrodermal activity sensors, blood flow sensors, heart rate sensors, photoplethysmographic sensors, humidity sensors, ultrasound sensors, analyte detectors, biometric sensors, or others. Furthermore, through software processing, the base can receive the information stored in the capsules over connectivity elements and transform it into a 2D or 3D digital image, a hologram or an animation, which can be seen directly on a screen, through other electronic devices connected through interactive multimedia technology, such as AR, MR and/or VR (FIG. 8).

Figure 7:
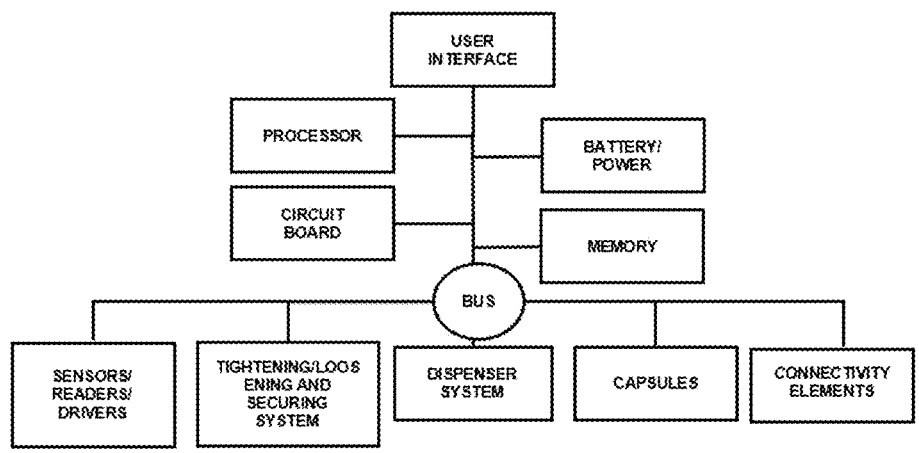
FIG. 7 Flow chart describing an example of connectivity and interoperability of the components of the wearable substance dispenser with interchangeable parts. Transfer of data, substances and power between components.

The base components can be inside it, housed in and/or connected to it, and/or partially integrated into it. The base (4—FIG. 1) of the device includes a surface for battery charging (22—FIG. 3), such as a connector, contact, or contactless system for battery charging, which could be USB or wireless charging through a charger. In one example of the invention, wireless charging can involve magnetic induction through an induction coil built into the base and/or in specific housing. In another example of the invention, wireless charging can involve resonant magnetic induction. Through the processor, the base (4—FIG. 1) of the device can also receive information provided by the capsule and/or interchangeable display/control panel (FIG. 7) and/or connected independent electronic devices (mobile phone, tablet, laptop) (FIG. 8) and generate electronic instructions to personalise the information displayed on the display/control panel (1) and/or activate the substance dispensing system (FIG. 5, FIG. 6) and/or adjust the strap position (FIG. 4). Data can be transferred via a direct electrical connection, a wireless connection, or a combination of the two. The base (4—FIG. 1) of the device can be made of a polymer material, a composite material, wood, leather, metal or metal alloys, ceramic, glass, a combination of these, or any other material that is able to support the parts contained in the base.

Interchangeable display/control panel (1—FIG. 2) A triple magnetic connection system (12—FIG. 2) is used to connect and disconnect the display/control panel of the device screen, which is partially built into the base of the device (4—FIG. 2). This system allows for the exchange of capsules (8—FIG. 2), the differentiated power step from the device's battery, information from the motherboard of the device to the screen and vice versa, and information from the different sensors (FIG. 7) In turn, it makes it easier to replace the display/control panel (1—FIG. 2) and to personalise the appearance of the device, such as the attaching of an analogue watch. In short, the connection/disconnection and attaching/removal of the display/control panel (1—FIG. 2) from its base via a multifunctional connector is possible for the first time in a device. The connection (12—FIG. 2) involves a triple connector that can use the three channels simultaneously or independently. The electronic connection between the display/control panel (1—FIG. 1) and the motherboard can contain spring, slot and/or magnetic-type connectors. The interchangeable display/control panel (1—FIG. 2) can contain LCD, OLED or similar technologies. In some versions of the invention, the display/control panel (1—FIG. 2) may include a touch screen, a flexible panel, a digital watch, a gaming platform, a remote control for other electronic devices, a real-time information communication or display platform for users (weather, time, skin, physiological and/or environmental parameters, holograms, etc.). The interchangeable display/control panel (1—FIG. 2) can be operated in combination with the base of the device, or with another independent device. In other versions of the invention, the recess (11—FIG. 2) where the display/control panel is connected (1—FIG. 2) along with the connection (12—FIG. 2) can be used to connect other types of mechanical, electronic or decorative devices other than a display/control panel, such as a holographic screen, items of jewellery, watches, fashion jewellery, or any ornamental or technological element.

Dispenser system (diffuser/atomiser) (FIG. 5, FIG. 6). The dispenser system (diffuser/atomiser) allows for smart, personalised control of the release of the substance or substances contained in the interchangeable capsules (5, 8—FIG. 1) through different spray modes: DIRECT MODE through an electromagnetic atomisation system (FIG. 5) or INDIRECT MODE through an ultrasound diffusion system (FIG. 6). The device can generate electromagnetic fields and/or ultrasound waves through the connections (14, 15a, 15b—FIG. 1; 26—FIG. 4) built into the straps, into the stator and into the track, the processor, the integrated circuit and software, and dispense (diffusion/atomisation) the substances.

The electronic dispenser system (diffuser/atomiser. FIG. 5, FIG. 6) can be activated automatically using the display/control panel (1—FIG. 1), in response to a stimulus detected by one or several sensors, using a switch, via another remotely connected electronic device (FIG. 7), or in combination with a manual dispenser system.

The function of the atomisation system (FIG. 5) is to release the substance contained in the interchangeable capsule (8—FIG. 1) specifically onto a discreet surface or recess, and is located in the secondary strap (3b—FIG. 5). The function of the diffusion system (FIG. 6) is to release the substance into the atmosphere almost continuously, over time intervals, or continuously. This can be located in the base, in the primary strap (3a—FIG. 6) or the secondary strap, or in the capsule itself (5—FIG. 6). The strap can incorporate connection wires or contain a system of non-added independent channels (14, 15a, 15b—FIG. 1) for the passing of electric pulses and the flow of substances between the base (4—FIG. 1) of the device and the dispenser system (diffuser/atomiser). In some versions of the invention, the conduits providing a transfer of data and electricity are obtained through the depositing, printing, moulding or injecting of channels containing semi-conductor, conductor or inorganic semi-conductor polymers, doped nanoparticle materials, nano-materials, or a combination of them. In some versions of the invention, the dispenser system (diffuser/atomiser, FIG. 5, FIG. 6) and the strap where it is connected can incorporate an electric connector (such as a spring-type mechanism) and a connection system (e.g. click connection, magnetic clasp or similar) to attach and remove the dispenser system (diffuser/atomiser) from the strap. In addition, the electrical connections (14, 26—FIG. 4) of the atomiser and the strap allow for sensors to be fitted to it, and new functions can therefore be added to the device, such as biometric sensors, as a safety system. In other versions of the invention, the modular atomisation system allows for special atomisers with nozzles for specific applications (nasal, oral, ophthalmic application, etc.) to be connected.

Tightening/loosening and securing system (FIG. 4). The ends of the straps (3*a*, 3*b*—FIG. 4) contain a tightening/loosening and securing mechanism. The tightening/loosening system is equipped with actuators (24, 25—FIG. 4) in the form of an electronic, mechanical, magnetic, piezoelectric, and/or geared linear motor that allows for one strap to be moved over the other and for the straps to adapt automatically and intuitively to a body and in preset positions. The securing mechanism contains a strap-based, click and/or magnetic strap attaching system. The electricity and the transfer of data required for the tightening/loosening and securing mechanism to work correctly is supplied through connections (14—FIG. 6) in the form of conduits inside the strap (3*a*—FIG. 6). The battery supplying the power can be contained in the base (4) or the strap (3*a*). The device tightening/loosening system can be based on the movement of the secondary strap (3*b*—FIG. 4) as the moving part over the primary strap (3*a*—FIG. 4) as the stationary part, or on the movement of the primary strap (3*a*—FIG. 4) as the moving part under the secondary strap (3*b*—FIG. 4) as the stationary part. In one example, the user can save three or more positions and activate them by pressing a switch or using the display/control panel (1) of the device, or in automatic response to the information received by one or several sensors (FIG. 7). The components of the tightening/loosening and securing system (FIG. 4) also contain a system (26—FIG. 4) for electronic connection among them. This acts as a connector, contact and safety system for the electric circuit (switch).

Based on this structure, the invention foresees an operating method of the wearable device (FIG. 9) in order to dispense one or several substances contained in one or several interchangeable capsules, which includes the following operational phases: connection of the interchangeable capsule(s) to the wearable dispenser; generation of electronic information based on data obtained from an interface: receipt of electronic information in the processor of the device; generation of an electronic instruction to activate the dispenser system; and the timely activation of the system to dispense substances from the wearable to spray and release the substance(s) in DIRECT and/or INDIRECT MODE.

In some versions, the electronic information received in the processor can also generate electronic instructions with additional functions, such as the personalisation of the information of a user interface, and interaction with the user and/or with other devices or users. For example, the capsule fitted in the device can send electronic information to the processor via connectivity elements, and this information is then processed as an electronic instruction to personalise the information displayed on the display panel. In another example, data from a pH sensor can be received and processed in the processor, leading to an electronic instruction to emit a specific tactile signal to the user of the need to dispense substance.

In other versions, the electronic information received in the processor of the wearable dispenser can generate electronic instructions to temporarily activate any element of the wearable dispenser, such as the particle propellant system and the tightening/loosening and securing system.

The following description of the preferential version of the invention and/or of any structural part thereof, as explained in this patent, gives an indication as to how they are at least configured in this way, but they can also be configured in a different manner that is not included in this description.

The device of the invention is made up of the following removable and interchangeable parts (see FIG. 1): one base (4 in FIG. 1), one or several interchangeable capsules (5 and 8 in FIG. 1), one interchangeable display/control panel (1 in FIG. 1), one or several straps (3*a* and 3*b* in FIG. 1) that tighten or loosen the device on the user, and one dispenser system (diffuser/atomiser) (FIG. 5, FIG. 6) The dispensing method of the device means that one or several substances contained in the interchangeable capsules can be dispensed via several dispensing mechanisms once personalised electronic instructions have been given (FIG. 9). The device contains the hardware and software to automate and control the release (dosage and frequency) of the substance(s) contained in the interchangeable capsules, and the displacement of the particles in the atmosphere. These diffusion and atomisation mechanisms (FIG. 5, FIG. 6) can be activated using the device or using other devices over a wireless connection, or in response to the information received from the interface, sensors or capsules (FIG. 9). The device includes an innovative, new connection system (12 in FIG. 1) between the base (4) and the display/control panel (1). This connection means that the display/control panel can be connected to/disconnected from the base. The base (4) also allows for the transfer of information and power between the processor, battery, screen, interchangeable capsule(s) (5, 8), and other parts of the device (FIG. 7), or even with other independent electronic devices, offering users a more effective usage and increased user-device or user-user interaction (FIG. 8). Furthermore, the device contains an electronic strap tightening/loosening and securing system (FIG. 4) that provides users with personalised adjustment of the size of the strap for an optimum user experience, thus enhancing the functionality of the dispenser system (diffuser/atomiser) of the device and sensors. FIG. 7 and FIG. 9 show an example of the system and method, indicating the interoperability and capacity of its parts and subsystems in exchanging and using the exchanged information.

The following are the preferential versions of the electronic dispensing modes for the substances contained in the interchangeable capsules of the device.

Atomisation system (DIRECT MODE). Electromagnetic system that allows for substances to be sprayed through an actuator (spray) using the repulsion/attraction action of electromagnets and permanent magnets, controlled using software and an electronic connection from the motherboard/battery and through connections (14—FIG. 5, 26—FIG. 4) in the strap to the atomiser. In a specific version (FIG. 5), a negative or limpet electromagnet (30) located on the atomiser mount applies attracting force to a permanent magnet (31) located on the atomiser unit (29) (standby position, A). The current supply causes a change in polarity in the electromagnet (30), repelling the permanent magnet (31) and, in turn, moving the unit (29) towards the actuator (28) (dispensing action, B), this being in the opposite direction to the usual atomisation movement to date. In another version, the system forces the attracting of magnets/electromagnets located on the unit and actuator of the atomiser. This results in the instant attracting of the magnets, causing the unit to move towards the fixed actuator. In another version, the substance is atomised by way of a solenoid valve driven by a solenoid coil. Through the electricity supply, movement of the rod or piston can allow for the substance to flow to an intermediate reservoir and its return movement forces this same flow through the actuator. Alternately, the micro electromagnet solenoid valve (magnetic push-pull actuator) can move a piston/rod that applies pressure to the actuator and expels the substance through it.

Diffusion system (INDIRECT MODE) System that sprays substances using ultrasounds (see FIG. 6). In some examples, the spray mechanism may be based on spray systems that use surface or ultrasound spray acoustic wave technology. The system can be used for the direct or diffused and indirect application of the substance to be released. The mechanism transforms the electricity supplied by the battery into mechanical power in the form of vibrations via a transducer (33). The transducer (33) may include a piezoelectric substrate (glass, ceramic, polymer or any other material, such as LiNbO3, lead zirconate titanate, quartz), one or more transducers, and polymer and/or metal membranes (34). The substance (36) is sprayed when it is subjected to the ultrasound waves (35) once in contact with the transducer. The ultrasound transmitter, which is capable of transmitting frequencies (between 20 kHz-100 MHz, preferably frequencies close to 100 KHz) may be submerged in the substance in liquid state, exposed to the incident of the liquid flow, or be touching a polymer that is sensitive to ultrasound stimulation. The substance may be contained in a recess, fall in a controlled manner onto the sprayed surface, or be absorbed by a polymer matrix (e.g. absorbed by ethylene-vinyl acetate, polyhydroxyethylmethacrylate, cellulose-type polymers, etc.). The substance flow may be controlled by a solenoid valve, a small pump, or carried by gravity or pressure differences. Dispensing can be controlled by the flow of the liquid, by the frequency of the ultrasound wave, or by a porous membrane. This ultrasound transmitter provides a controlled spray in terms of time, volume, and spatial distribution of the substance. This mechanism can be equipped with different pressure and volumetric valves, membranes, piezoelectric materials, or other control methods.

Software can be used to programme the atomisation/spray time, activate the electromagnet and valve changes, piezoelectric materials and membranes, and control the intensity and frequency of the pulses emitted. The electromagnet system and the ultrasound system may incorporate a motor and/or tactile sensor and/or ultrasound transducers (see FIG. 6 32, 33) to expel the particles of the sprayed substances into the atmosphere using changes in air pressure (pressure waves) at a greater or lesser speed, through the direct or indirect emission channels of the dispenser system (see A, B, C in FIG. 6). This or another motor and/or tactile sensor (32) also mean that a pulse or vibration on the user's skin can be used to configure, personalise or control this vibration, this being the coding of a substance and image to the feeling of touch. The transmitter/tactile sensor may also include the function of user notification/alert, e.g. of the need to activate the dispenser system. Examples of motors or tactile sensors may include a linear resonant actuator, a eccentric rotating mass actuator or a piezoelectric substrate.

The following are the preferential versions of the tightening/loosening and securing system modes for the device:

In a preferential version of the invention, the primary strap (3*a*—FIG. 4) may contain one or several actuators (24—FIG. 4), in the form of electromagnets, and electrical connections (14—FIG. 4) so that the device can be programmed to alternate the polarity of the magnetic field. In this same version, the atomiser mount (23—FIG. 4) on the primary strap incorporates one or several actuators (25—FIG. 4) in the form of permanent magnets, with alternate polarities. The movement takes place through electric pulses received by the electromagnets that control the polarity and intensity of the magnetic fields generated in the stator. The forces of attraction and repulsion between the magnets force the movement of the secondary strap (FIG. 4, tightening movement A and loosening movement B). In another version of the invention, a motor built into the primary strap can drive a rack and pinion-type gear system. This system is designed to minimise friction between the parts. In another version of the invention, the primary strap can move the secondary strap using the inverse piezoelectric effect (linear ultrasound piezoelectric motor). The primary strap may contain a piezoelectric material to which the appropriate electrical signal is applied, resulting in its deformation and, in turn, in the deformation of a built-in elastic material. The mechanical movement is the result of the force of friction between the touching surfaces of the straps. In another version of the invention, the motor may contain one or several teeth that use friction to push the secondary strap and that act as a braking system when idle. The strap material may be made of synthetic or natural leather, polymer material, metal or alloy, composite materials, fabrics, a combination of the aforementioned, or other materials.

In a preferential version, the electronic connection (26—FIG. 4), located partially on the parts (6, 23—FIG. 4) forming the tightening/loosening and securing system, allows for power and data to be transferred to the spray system (DIRECT MODE, FIG. 5) through a series of contacts. In turn, it acts as a safety system for the electric circuit, enabling or preventing the flow of current when the straps are closed or open, respectively. The connection (26—FIG. 4) may be a manual, electric, electronic and/or magnetic switch.

The device, the methods, the systems described and/or claimed in this document may be produced and developed without experimentation due to the extent of this description. While the devices, systems and methods of this invention have been described in terms of specific versions, it will be clear to experts in the field that variations can be applied to the devices, systems and/or methods in their steps or in the sequences of steps of the method described in this document without diverging from the concept, spirit and scope of the invention. All these replacements and similar modifications for experts in the field are considered as part of the spirit, scope and concept of the invention, as defined for the attached claims.

The term "holder" is understood in this document as the part or set of parts in the electronic device with the function of supporting, organising, connecting and also decorating and embellishing the interchangeable capsules.

The term "part" is understood in this document as the different components of the wearable substance dispenser device, which may be fixed or removable and that are connected to the device. They may also be autonomous in terms of power.

The term "incorporate" is understood in this document as the action of integrating non-interchangeable parts.

The term "base" is understood in this document as the physical mount where the interchangeable capsule and the interchangeable display/control panel are connected, and that may contain the necessary electronic components for the functionality of this device (processor, battery, motherboard, integrated circuit for the transfer of information and power, etc.).

The term "screen" is understood in this document as the set of parts that enable it to operate and that include a display panel, integrated circuits, controls and mount.

The term "display/control panel" is understood in this document as the part of the screen that contains at least one front protective surface, a touch screen or digitiser, an OLED or LCD panel, and a rear mount.

The term "straps" is understood in this document as the parts of the system that allow for the wearable to be adjusted to a body and are, in turn, the physical mount for the tightening/loosening and securing system of the device and of the spray/atomisation systems, and physical connection, electronics and fluid system between the system parts (bus).

The term "wearable substance dispenser device" is understood in this document as the set of parts that contain the electronic, mechanical and substance flow circuits required to dispense substances contained in the interchangeable capsules either autonomously or at will.

The term "substance" is understood in this document as any element capable of being stored inside the interchangeable capsules in liquid, solid or gaseous state, or a combination of these states, and that is capable, once the interchangeable capsule is connected to the device, of flowing along connection channels in the device to reach the dispenser system (spray/atomisation) to be released into the atmosphere in line with any of the spraying modes described in this document.

The term "connection" is understood in this document as the electrical, data, fluid, physical, or wireless link, or a combination of the aforementioned.

The term "spray" is understood in this document as the action of transforming a substance in particle and/or droplet form into fine mist or vapour.

The term "diffusion" is understood in this document as the combination of the actions of spraying and dispersing the substance in the environment.

The term "operative link" is understood in this document as the physical or logical link between parts, devices and/or combinations thereof to fulfil a specific role.

The term "device security system" is understood in this document as the mechanism that prevents the wearable from being used illegitimately, that prevents accidental leakage from the device after it has been correctly secured and connected, and that allows for the flow of power to any part of the device to be opened or closed.

The term "user interface" is understood in this document as the medium (physical or logical) of the wearable for the interaction of one or several users with this device.

The term "bus" is understood in this document as the set of conductors and channels in the device to distribute power, information, and substance flow between the parts of the device.

The invention includes:

(1) A wearable substance dispenser device with interchangeable parts that comprises.
  a. at least one interchangeable capsule (5, 8) containing at least one substance and operatively linked to a processor and/or a base (4), and/or to straps (3a, 3b) and/or to a substance dispenser;
  b. the processor programmed to receive electronic information, generate and send an electronic instruction to temporarily activate one or several parts connected to the device,
  c. the base (4) to which the interchangeable capsule (8) is connected and that supports an interchangeable display/control panel (1) in a recess (11) and that, in turn, includes sensors, readers, data, power and wave storage and transmission systems, and is operatively linked to the processor and/or the parts connected to the wearable dispenser device;
  d. the substance dispenser system operatively linked to the interchangeable capsule(s) (5, 8) and to the processor, and that includes at least one electronic particle dispenser and/or spray and/or propellant mechanism;
  e. the interchangeable display/control panel (1) operatively linked to the processor and the base (4) through temporary connections (12), so that it secures the interchangeable capsule (8) and acts as a user interface and/or information display;
  f. the primary strap (3a) configured to secure the wearable dispenser to a body and that operatively links the base (4), the processor and the interchangeable capsules (5, 8) to the parts connected to that strap (3a) and/or another strap via a bus and integrated connections (14, 15a, 26);
  g. the secondary strap (3b) configured, along with the primary strap (3a), to secure the wearable dispenser to a body and, in turn, operatively link the interchangeable capsule (8) to the parts connected to that strap (3b) via integrated connections (15b);
  h. at least one connector (2) operatively coupled and connected to the primary strap (3a) and/or the secondary strap (3b), and/or the base (4) and/or the interchangeable capsule(s) (5, 8),
  i. a tightening/loosening and securing system operatively linked to the processor, the base (4), the dispenser system, the primary strap and the secondary strap (3a, 3b), and that activates the movement of at least one of the straps (3a, 3b).

(2) The device (above) characterised because the interchangeable capsule(s) (5, 8) include at least one material configured to provide the mechanical and chemical strength required to store the substance.

(3) The device (above) characterised because the interchangeable capsule(s) (5, 8) are solid and/or hollow and include at least one compartment with a volume to hold 0.1-100 millilitres.

(4) The device (above) characterised because the interchangeable capsule(s) (5, 8) are operatively linked at least to a fluid circuit in the base (4) and/or in the straps (3a, 3b) and/or in the dispenser system through an adaptor with a combined substance flow closure function, anti-drip valve and/or connector.

(5) The device (above) characterised because the interchangeable capsule(s) (5, 8) is operatively linked to the processor by way of means of electronic identification and/or connectivity parts (RFID, NFC chips or similar technologies) configured to send unique operational and identifying electronic information from the interchangeable capsule(s) to the processor, which will then generate electronic instructions to temporarily activate the parts of the device and/or of other devices.

(6) The device (above) characterised because the interchangeable capsule(s) (5, 8) contains substances in liquid, solid or gaseous state, or combinations of substances in said states.

(7) The device (above) characterised because the interchangeable capsule(s) (5, 8) is functionally available on other mounts outside the device, provided these mounts have the necessary minimum components for its connection.

(8) The device (above) characterised because the base (4) is made of at least one material configured to provide the function of support for the parts partially integrated and/or housed and/or contained and/or connected to said base.

(9) The device (above) characterised because the base (4) also connects the processor and an electronic control circuit of the device, and because the processor and the electronic control circuit are configured to use software to control the dispensing of the substance (programming of the manner, the time and the frequency of release, programming of release by GPS or other parameters, or a combination of the aforementioned).

(10) The device (above) characterised because the sensors of the base (4) are formed by biometric sensors, pH sensors, temperature sensors, electrodermal activity sensors, blood flow sensors, heart rate sensors, photoplethysmographic sensors, humidity sensors, ultrasound sensors, analyte sensors, and/or sensors of a similar nature, configured to gather data from the user and/or the environment and then send it to the processor to generate adapted instructions.

(11) The device (above) characterised because the sensors and data and wave transmission parts of the base (4) are formed by touch-sensitive stimulus generating tactile transmitters and/or connectivity parts to provide notification/alert functions and/or device interoperability functions with the user, other devices and/or the environment using interactive multimedia technology.

(12) The device (above) characterised because the base (4) includes independent spaces sealed from the circulating flow of substances in the device and containing power storage and transmission parts, which include a battery and means for charging through a connector and/or a contact and/or a wireless connection by magnetic and/or resonant induction or similar technologies.

(13) The device (above) characterised because the connection (12) involves a multiple connector with slot and/or magnetic and/or spring coupling systems, and the recess (11) in the base (4) connect, operatively link the processor and the base to the interchangeable display/control panel (1) and enable it to operate, and/or can be functionally connected to other parts (mechanical, electronic and/or decorative).

(14) The device (above) characterised because the processor receives electronic information, generates and transmits one or several electronic instructions via a wireless or physical connection, or a combination of the two, and via connections of the same nature, and also operatively links said processor to the capsule(s) (5, 8) and/or the base (4) and/or the substance dispenser system and/or the display/control panel (1) and/or the tightening/loosening and securing system.

(15) The device (above) characterised because the straps (3a, 3b) are formed by at least one material configured to provide the support and bus function, and configured to provide the mechanical and chemical strength required for the substances and the flow running through them.

(16) The device (above) characterised because the tightening/loosening and securing system is formed by at least one motor and/or movement drive actuator for at least one of the straps (3a, 3b), which includes at least one mechanical and/or magnetic and/or electronic and/or piezoelectric-type configurable mechanism or a combination thereof and/or similar technologies.

(17) The device (above) in which the operative link of the tightening/loosening and securing system is formed by at least one temporary electrical connection (26) that acts as a safety system for the electrical circuit.

(18) The device (above) characterised because the dispenser system is formed so that its activation and substance dispensing can be controlled at will, by way of electronic programming, via the display/control panel (1), remotely from another device, or using a button.

(19) The device (above) characterised because the dispenser system is formed by a spray atomisation system (DIRECT MODE) operated by electromagnets.

(20) The spray atomisation system (above) characterised because the atomiser can be activated by movement of the unit (29) towards the actuator (28) or movement of the actuator (28) towards the unit (29).

(21) The device (above) characterised because the dispenser system is formed by a modular atomisation system that connects nozzles for specific applications (nasal, oral, ophthalmic, or of a similar nature) in which these nozzles send electronic control information to the processor, which generates an electronic instruction to adapt the operating of the dispenser system to a specific mode.

(22) The device (above) characterised because the dispenser system is formed by an ultrasound diffusion system (INDIRECT MODE) operated by one or several ultrasound transducers.

(23) The device (above) characterised because the particle propellant system of the dispenser system is formed by transducers and/or actuators and/or motors and/or other similar propellant systems configured to displace the particles released into the atmosphere.

(24) The device (above) characterised because the connections and connecting systems of the straps (3a, 3b), of the connectors (2), of the base (4), and of the dispenser system are of a magnetic and/or spring and/or slot-type nature and also include independent internal and/or extrinsic channels (15a, 15b) and the necessary means (valves, mixers, flow controllers, membranes) to combine and transport the substances contained in the interchangeable capsules (5, 8) and operatively link these capsules to said parts of the device.

(25) The device (above) characterised because the connections of the interchangeable capsule(s) (5, 8), of the straps (3a, 3b), of the connectors (2), of the base (4), of the dispenser system, and of the tightening/loosening and securing system are formed by conducts and/or wiring and/or contacts configured to provide data and/or electricity transfer through semi-conducting polymers and/or conducting materials and/or inorganic semi-conducting materials and/or composite materials and/or nanomaterials, or a combination thereof, and this configuration also operatively links the processor to said parts of the device.

(26) The device (above) characterised because the sensors are operatively linked to the strap(s) (3a, 3b) and/or to the dispenser system and the processor, and can obtain biometric data or data with similar characteristics based on which the processor generates electronic instructions to temporarily activate the parts of the device and/or of other devices.

(27) A method for dispensing at least one substance contained in one or several interchangeable capsules through a wearable dispenser, where the method involves at least the following operating phases:

a) connect the interchangeable capsules to the wearable dispenser;

b) once connected, generate electronic information from an interface based on data;

c) after generating the electronic information, send it to a processor in the wearable dispenser;

d) in response to the receipt of the electronic information, generate an electronic instruction to activate a substance dispenser system in the wearable dispenser; and e) in response to generating the electronic instruction, temporarily activate the substance dispensing system in the wearable dispenser to spray and release the substance.

(28) The method (above) which also includes, after the processor has received the electronic information, the generating of an electronic instruction to customise the information accessible over the interface of the wearable dispenser and/or other devices.

(29) The method (above) characterised because the electronic information is generated from the interface based on data from the interchangeable capsules.

(30) The method (above) which also includes, after the processor has received the electronic information, the generating of an electronic instruction to encode the information from the interchangeable capsules into pulses and/or vibrations on the user's skin as a notification/alert via motors and/or tactile sensors.

(31) The method (above) characterised because the electronic information is generated from the interface based on data from sensors in the wearable dispenser and/or from another device.

(32) The method (above) which also includes, after temporarily activating the substance dispenser, the activation of a propellant to spray the substance into the atmosphere.

(33) The method (above) which also includes, after the process of the wearable dispenser has received the electronic information, the generating of an electronic instruction to activate a tightening/loosening and securing system to adapt the position of the straps together.

(34) The method (above) characterised because the electronic information is generated from the user interface of the wearable dispenser and/or another device.

(35) The method (above) characterised because the temporary activation of the substance dispenser involves the spraying of said substance by atomisation.

(36) The method (above) characterised because the temporary activation of the substance dispenser involves the spraying of said substance by ultrasounds.

We claim:

1. A wearable substance dispenser device with at least one interchangeable capsule comprising:
    a. at least one interchangeable capsule (5, 8) containing at least one substance and electronically connected to a processor, a base (4), a plurality of straps (3a, 3b) comprising a primary strap and a secondary strap and a substance dispenser;
    b. wherein the processor within one of the base (4) or an interchangeable display/control panel (1) is programmed to receive electronic information, generate and send an electronic instruction to temporarily activate one or several parts connected to the wearable substance dispenser device;
    c. the base (4) to which the at least one interchangeable capsule (8) is connected and that supports the interchangeable display/control panel (1) in a recess (11) and comprising sensors, readers, data, power and wave storage and transmission systems, and is electronically connected to the processor and to the one or several parts connected to the wearable substance dispenser device;
    d. the wearable substance dispenser device electronically connected to the at least one interchangeable capsule (5, 8) and to the processor, and that includes at least one electronic particle dispenser and a spray propellant mechanism;
    e. the interchangeable display/control panel (1) electronically connected to the processor and the base (4) through temporary connections (12), so that it secures the at least one interchangeable capsule (8) and acts as a user interface information display;
    f. the primary strap (3a) configured to secure the wearable substance dispenser device to a body and that electronically connects the base (4), the processor and the at least one interchangeable capsules (5, 8) to one or several parts connected to the primary strap (3a) via a bus and integrated connections (14, 15a, 26);
    g. the secondary strap (3b) configured, along with the primary strap (3a), to secure the wearable substance dispenser device to a body and electronically connecting-the at least one interchangeable capsule (5, 8) to one or several parts connected to the secondary strap (3b) via integrated connections (15b);
    h. at least one connector (2) operatively coupled and connected to at least one of the primary strap (3a), the secondary strap (3b), the base (4) and the at least one interchangeable capsule (5, 8);
    i. a tightening/loosening and securing system electronically connected to the processor, the base (4), the wearable substance dispenser device, via electronical connections through the primary strap and the secondary strap (3a, 3b), and that activates a movement of at least one of the primary strap and the secondary strap (3a, 3b),
    j. wherein the sensors consist of one or more of a pH sensor, a temperature sensor, an electrodermal activity sensor, a blood flow sensor, a heart rate sensor, a photoplethysmographic sensor, a humidity sensor, an ultrasound sensor, an analyte detectors, and a biometric sensor,
    k. wherein the readers consist of one or more of an RFID reader and a NFC reader,
    l. wherein the data system consists of one or more of a direct electrical connection and a wireless connection,
    m. wherein the power system consists of one or more of a connector, contact, or contactless system for battery charging, comprising one or more of a USB charging system and a wireless charging system comprising one or more of built-in magnetic induction and resonant magnetic induction,
    n. wherein the transmission system consists of one or more of a telephone antenna, a microphone, a speaker, a tactile device, and an RFID reader.

* * * * *